United States Patent [19]
McLees

[11] Patent Number: 5,334,158
[45] Date of Patent: Aug. 2, 1994

[54] AUTOMATIC NEEDLE TIP GUARD FOR STANDARD HYPODERMIC NEEDLES

[76] Inventor: Donald J. McLees, 2623 Virginia Ave., Everett, Wash. 98201

[21] Appl. No.: 169,010
[22] Filed: Dec. 20, 1993
[51] Int. Cl.⁵ .............................. A61M 5/00
[52] U.S. Cl. ........................ 604/110; 604/198
[58] Field of Search .......... 604/110, 192, 198, 263, 604/187

[56] References Cited

U.S. PATENT DOCUMENTS 5,059,180  10/1991  McLees .......................... 604/110
5,092,851  3/1992  Ragner ....................... 604/263 X
5,092,852  3/1992  Poling ............................ 604/192
5,104,384  4/1992  Parry ............................ 604/192

Primary Examiner—John D. Yasko

[57] ABSTRACT

A small bead-like automatic guard for the tip of a standard one-time use hypodermic needle which initially resides near the needle tip and becomes activated by movement of the guard away from the tip due to insertion of the needle through the skin. At withdrawal a coil spring in conjunction with the guard's internal, mechanism automatically locks the guard over the needle tip.

5 Claims, 10 Drawing Sheets

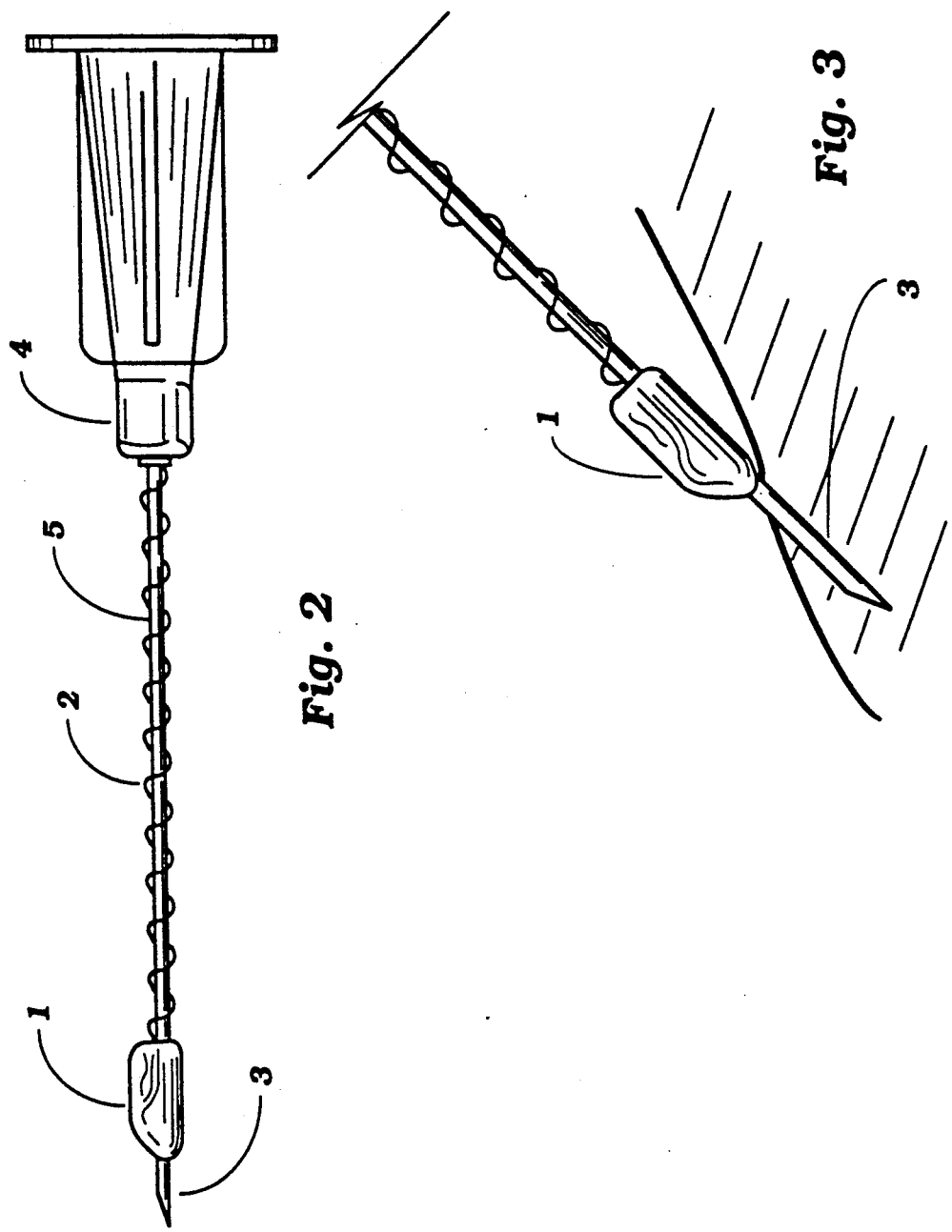

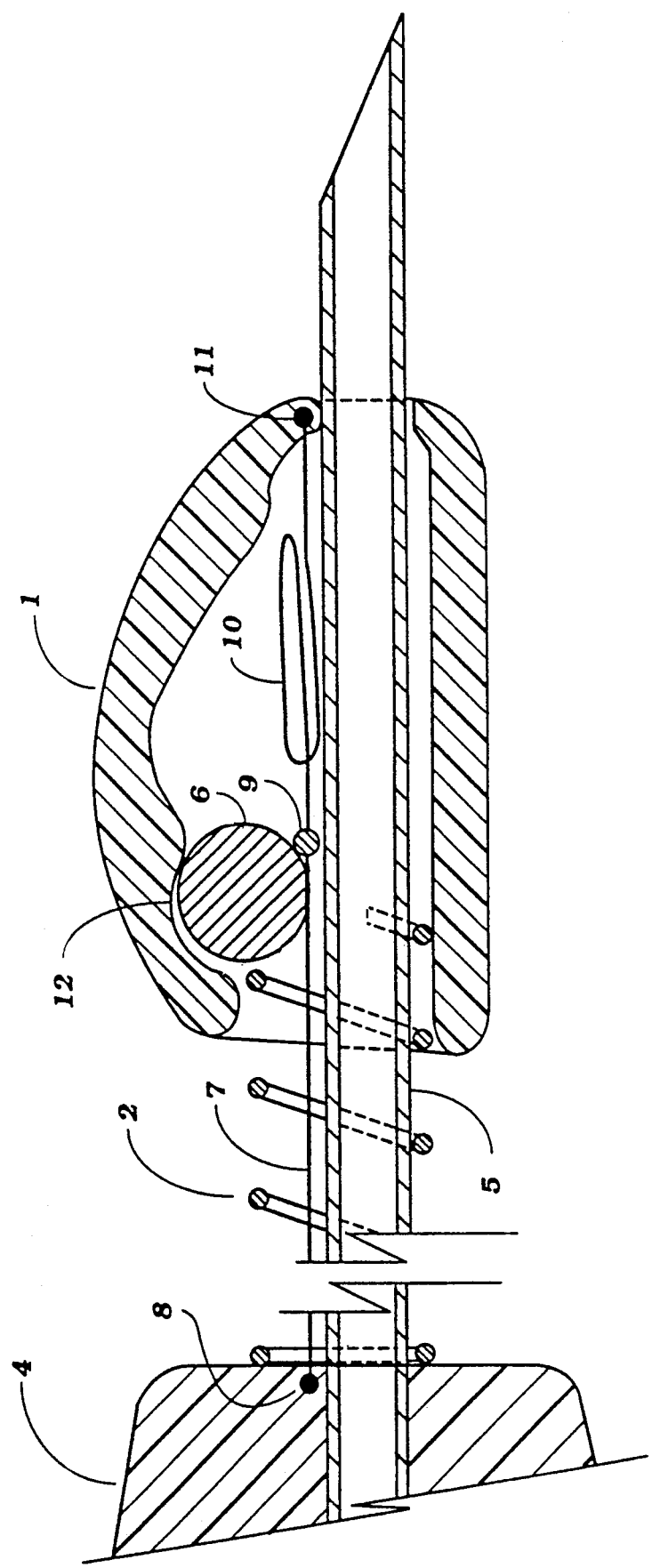

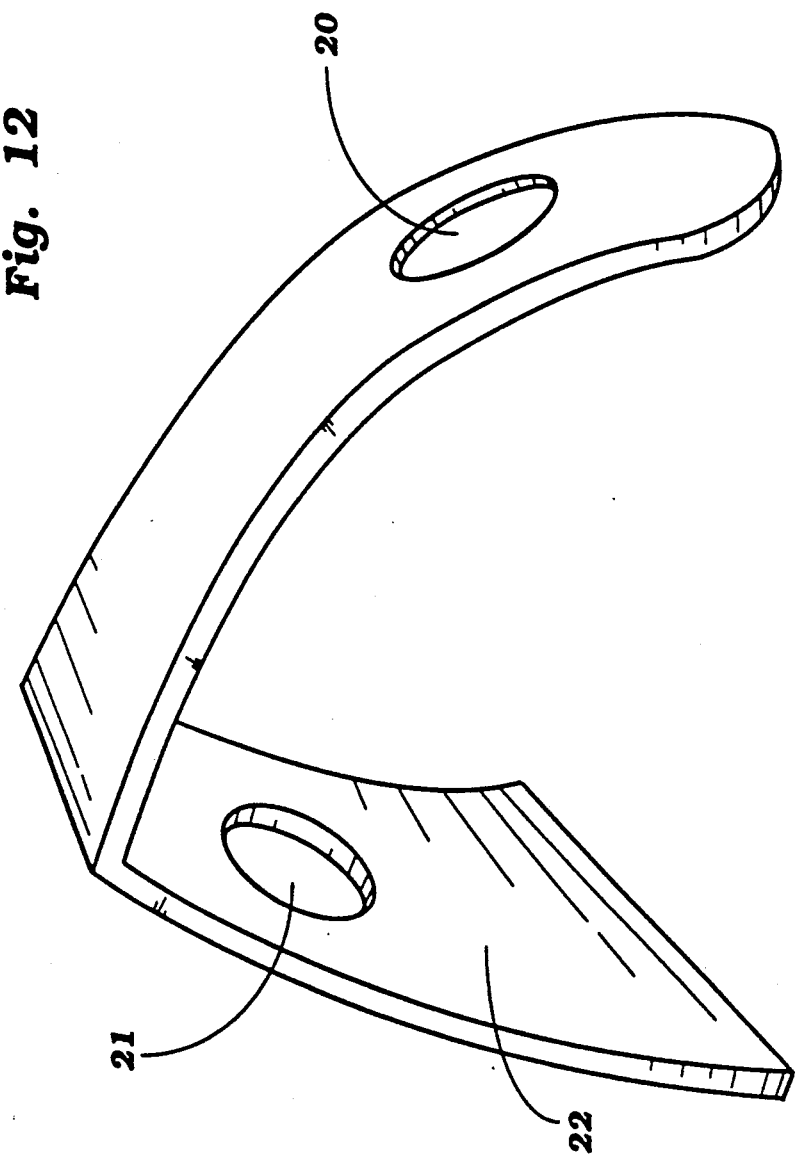

AUTOMATIC NEEDLE TIP GUARD FOR STANDARD HYPODERMIC NEEDLES

BACKGROUND OF THE INVENTION

1. Field of the Invention

This invention relates to medical instruments. It applies specifically to disposable hypodermic needles and in the U.S. Patent Office it would be found in a classification for needle tip guards which protect health care workers from accidental needle sticks.

2. Description of the Prior Art

The need for protection of health care workers from infectious diseases such as hepatitis and AIDS due to accidental needle sticks by now has been well documented. A preponderance of devices have evolved for single use hypodermic needles which either provide a protective cover for the needle tip after usage or withdraw the needle back up inside the syringe. Unfortunately the vast majority of these devices have inherent drawbacks which render them unsuitable as practical products. Most are unduly complex, bulky, cumbersome and quite costly in relation to the low cost of manufacture for simple needles and their attached hubs. Perhaps the most common disadvantage of almost all existing guards and protection systems is that they require something additional from the user beyond what is required for normal operation.

The ideal guard should be simple and yet positively locking in both directions such that it prevents the needle tip from escaping while keeping itself locked onto the needle. It should be very low cost which means using little material, using the very bare minimum of preferably standard parts, and configuring the guard for use with standard hypodermic needles. That is, the guard should not require that the needle be modified for proper operation. Since needles are usually made by totally automated machines, the cost of needle modification could make such a guard cost prohibitive. Also, the ideal guard should be entirely automatic. Any needle which requires additional effort or operational steps to use would be resisted by the medical community, and any needle guard which must be manually activated stands a good chance in many situations of not being used at all. This would be especially true in emergency situations where the possibility of accidents is already higher anyway.

Some of the devices of the prior art such as an invention by Vaillancourt (U.S. Pat. No. 4,804,371) issued in 1989 can be examined in light of the desirable characteristics of an ideal guard. One embodiment of the Vaillancourt guard shows a cap extended over the needle tip by a spring. The cap does not positively lock and the mechanism must be manually activated after the needle is used. Another embodiment, an accordian-like sheath, must be manually extended and is relatively bulky.

A later device by Martin et al. (U.S. Pat. No. 4,887,998) provides a partial sleeve on a spring and an occluding ball trap which prevents the tip from exiting but does not prevent motion in the other direction and thus the guard does not positively lock. This mechanism must also be manually activated and is unduly complex and costly.

Inventions of Sudnak (U.S. Pat. No. 4,894,055) and Paris (U.S. Pat. No. 4,911,693) both provide spring loaded total sleeves which entirely enclose the needle. They are bulky, costly and must be manually activated.

The other family of protective devices provide for retraction of the needle up into the syringe body or an extension of the syringe after usage. These devices require highly modified syringes or highly modified syringe/needle combinations and are quite complicated and therefore costly. Attempts have been made to minimize the extra motion or effort required to activate these devices. The Vadher needle (U.S. Pat. No. 4,946,446) retracts when the syringe plunger is pushed once again after use, so activation is still not entirely automatic and may not occur at all if the operator is unfamiliar with the particular mechanism or is in a hurry.

The Lennox needle (U.S. Pat. No. 4,966,593) retracts when the plunger is pushed all the way down. This makes the device impractical for using the plunger to fill the syringe (such as in drawing blood or drawing medication from another container) and still does not guarantee that the mechanism will be activated.

Unique to the guards in this survey of the prior art is a device of this inventor (McLees, U.S. Pat. No. 5,059,180) which issued in 1991. It consists of a spring and a small bead-like guard which resides initially near the needle tip and which becomes activated when the skin pushes the guard back from the tip at insertion. Thus it is the act of insertion which activates the guard and normal usage of the needle guarantees that activation must automatically occur. The guard is also simple, low cost and positively locking. However, it requires a special needle with a raised shoulder. From the standpoint of potential manufacturers this fact makes the needle cost prohibitive. Obviously it would be desirable to have a guard similar in concept which can be used with a standard needle.

SUMMARY OF THE INVENTION

It is the object of this invention to provide a simple, low cost and automatically activated hypodermic needle tip guard which can be added to conventional disposable hypodermic needles. A further object is to have the guard be positively and irreversibly locking such that once the guard is automatically positioned over the needle tip, the tip cannot penetrate the guard and the guard cannot easily be pulled off the needle tip. A still further object is to have the guard be universally applicable to all single use hypodermic needles whether they be used for the injection of medications or the withdrawal of fluids as in blood drawing.

The accomplishment of such objectives can be achieved in two basic ways. The mechanism must either be responsive to the distal pointed tip of the needle or to a fixed point located somewhere proximal of the tip. For that reason two alternative mechanisms are herein presented. Since one alternative uses a reference point on the hub from which the needle protrudes, it is referred to as hub responsive. The other alternative is tip responsive. The choice of which device should be manufactured may depend on marketing and economic considerations which are not pertinent to this description.

Both alternatives rely on a compressed coil spring around the needle and extending from the hub to the guard for automatic placement of the guard upon needle withdrawal. Both have the guard initially placed near the needle tip at a location far enough away so as to not interfere with drawing medication from a container or with needle insertion but close enough to guarantee that insertion causes the guard to move back and thus activate the mechanism.

The preferred embodiment of the hub responsive alternative uses a small wire attached to an anchor point on the hub at one end and to a point inside the guard on the other end. Also attached to the wire is a small stop between the two anchor points and initially wedged between a ball and the surface of the needle inside the guard. The guard is held in its initial position by the tension of the anchor wire between the hub and wedged stop pulling against the force of the compressed spring. The internal configuration of the guard allows the wedged stop and ball to be released when needle insertion moves the guard back. Upon needle withdrawal the spring pushes the guard over the end of the needle while also pushing the ball in front of the tip and thereby blocking the tip from exiting the guard. The anchor wire prevents the guard from coming off the end of the needle.

The preferred embodiment of the tip responsive alternative uses a ball wedged between the needle and an inside surface of the guard to hold the guard in its initial position. Movement of the guard back at needle insertion releases the wedged ball. Upon needle withdrawal the coil spring pushes the guard over the end of the needle. A secondary spring inside the guard is released when the needle tip enters the guard. The secondary spring then occludes the distal guard opening thus preventing exit of the tip while simultaneously pushing the ball back into a wedged relationship between the guard and needle and thereby locking the guard on the end of the needle. Any force in the direction of pulling the guard off the needle end causes the wedged ball to tighten even more in the same manner as a oneway roller clutch.

BRIEF DESCRIPTION OF THE DRAWINGS

FIG. 2 is an enlarged side view of just the needle and hub with attached guard and spring.

FIG. 3 is a side view of the needle penetrating the skin which is shown in cross section.

FIG. 4 is a side view center line cross section of the needle, the spring, a portion of the hub and the hub responsive guard.

FIG. 12 is an isometric drawing of an alternative secondary spring.

DETAILED DESCRIPTION OF THE DRAWINGS

Figure 1:
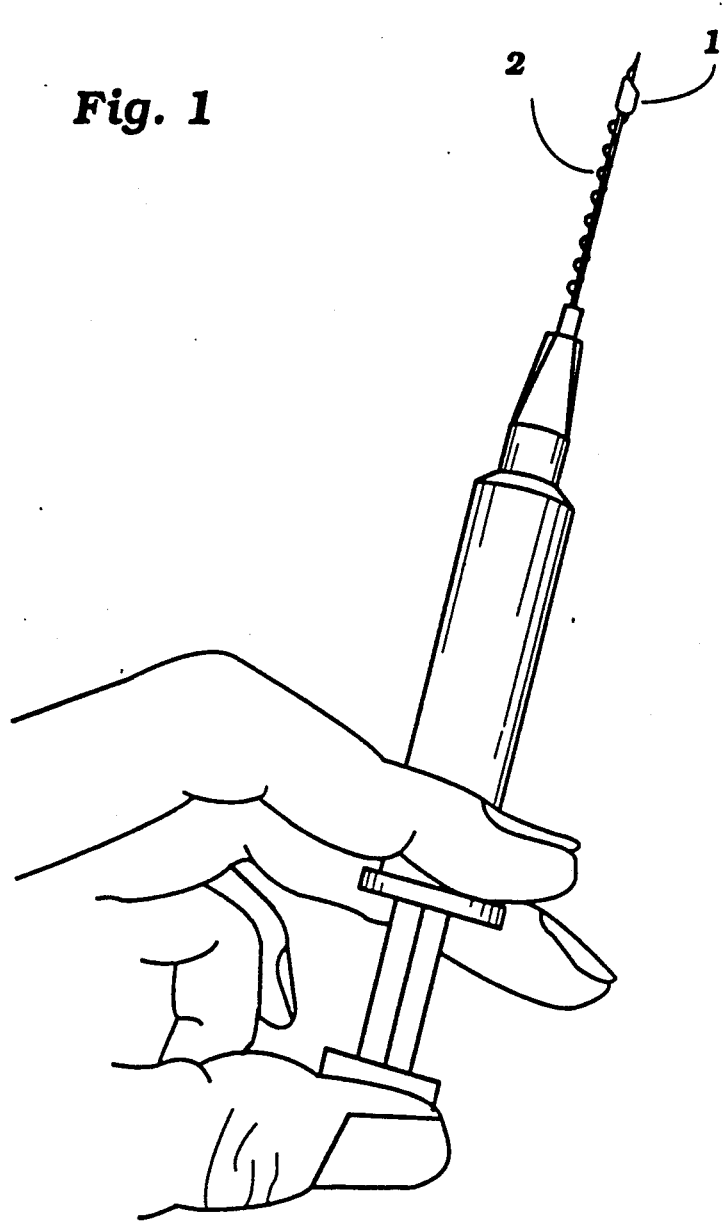
FIG. 1 shows a typical standard hypodermic syringe and needle assembly with the attached coil spring and needle tip guard.

FIG. 1 is illustrative of a conventional syringe with the attached needle. Surrounding the needle is coil spring 2 and needle tip guard 1.

In FIG. 2 the coil spring can be seen extending from the guard 1 to the hub 4 of a standard needle/hub combination. The guard is shown locked in its initial position around the needle shaft 5 and back somewhat from the needle tip 3.

It can be seen in FIG. 3 that the guard 1 has been pushed back from its initial position by insertion of the needle tip 3 through the skin.

The side view cross section of FIG. 4 shows the guard 1 in its initial position on the needle shaft 5. The spring 2 is compressed between the hub 4 and a ball 6 inside the guard. An anchor wire 7 is in tension between an anchor point 8 on the hub and a stop 9 attached to the wire and wedged between the ball and the surface of the needle. A slack portion 10 of the wire is coiled inside the guard and extends from the stop to an anchor point 11 at the front of the guard. The guard is held in place with the spring in compression and the wire in tension because the inside dimension between the needle and the guard wall at the guard back chamber 12 is less than the sum of the diameters of the ball and the stop. The spring cannot push the ball past the stop as long as the guard is in place.

Figure 5:
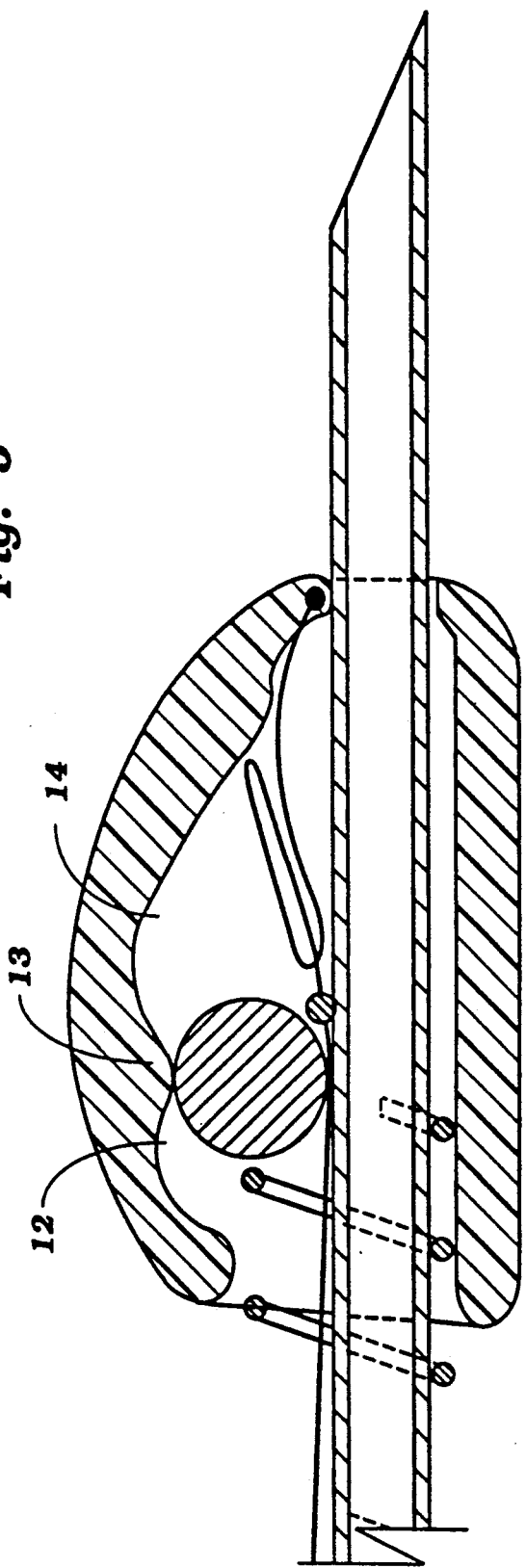
FIGS. 5,6 and 7 are side view center line cross sections of the hub responsive guard in various stages of operation.

FIG. 5 shows the guard as it would appear when pushed back slightly by the skin when the needle is inserted. The constriction 13 between the guard front chamber 14 and back chamber 12 forces the ball down against the tensioned wire. Since the internal space at the constriction is larger than the ball diameter, the ball is free to enter the front chamber as the guard continues back.

Figure 6:
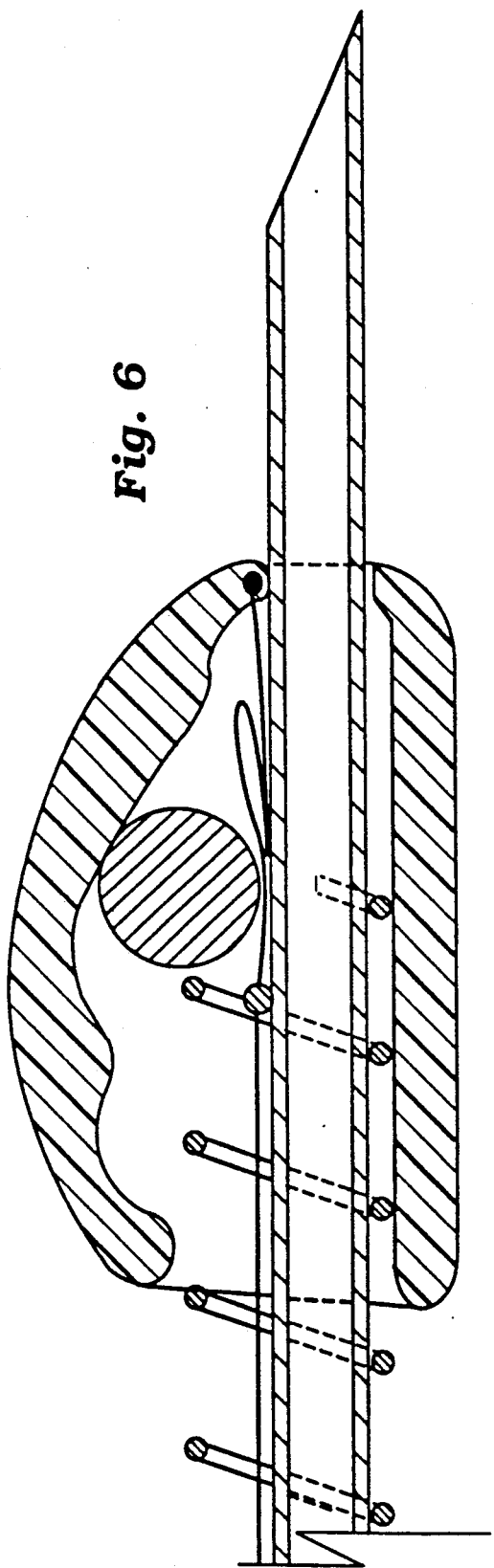

There is enough space inside the front chamber so that the spring can easily push the ball over the stop and against the guard front wall as shown in FIG. 6. When the needle is withdrawn the spring pushes the ball to the front of the front chamber while simultaneously pushing the guard over the needle tip.

Figure 7:
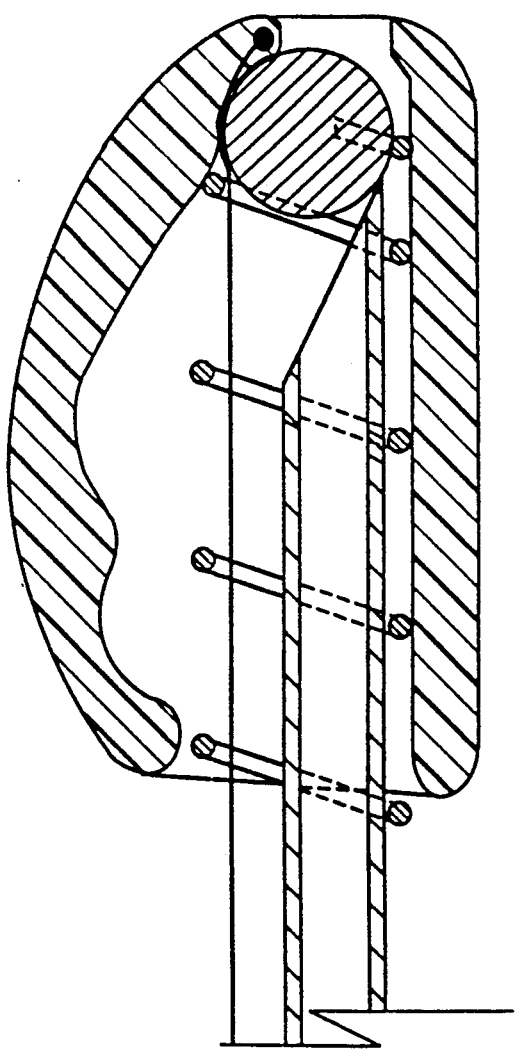

FIG. 7 shows the guard in its final position with the ball occluding the front opening. The entire anchor wire is in tension, the overall length having been chosen such that the guard is pulled to a stop by the wire just after the ball is pushed in front of the tip by the spring. The guard is thus effectively locked on the tip of the needle and with the proper selection of materials the needle should collapse before the tip would escape. Any force which pulls the guard off would have to be greater than the breaking strength of the wire, which would be quite substantial for steel.

Several different geometric shapes can be equally effective functionally as a stop 9. Its shape must keep it in place between the ball and needle while holding the wire in tension. For purposes of illustration in FIGS. 4 through 7 the cross hatched circle 9 can be assumed to be the center section of a "U" shape lying between the ball and needle. The stop could also be a ring around the bottom of the ball, a washer, two spherical beads (one on each side at the front of the ball) or even just a loop in a larger gage anchor wire. A detailed cost analysis beyond the scope of this functional description would be necessary to choose to optimum shape.

Figure 8:
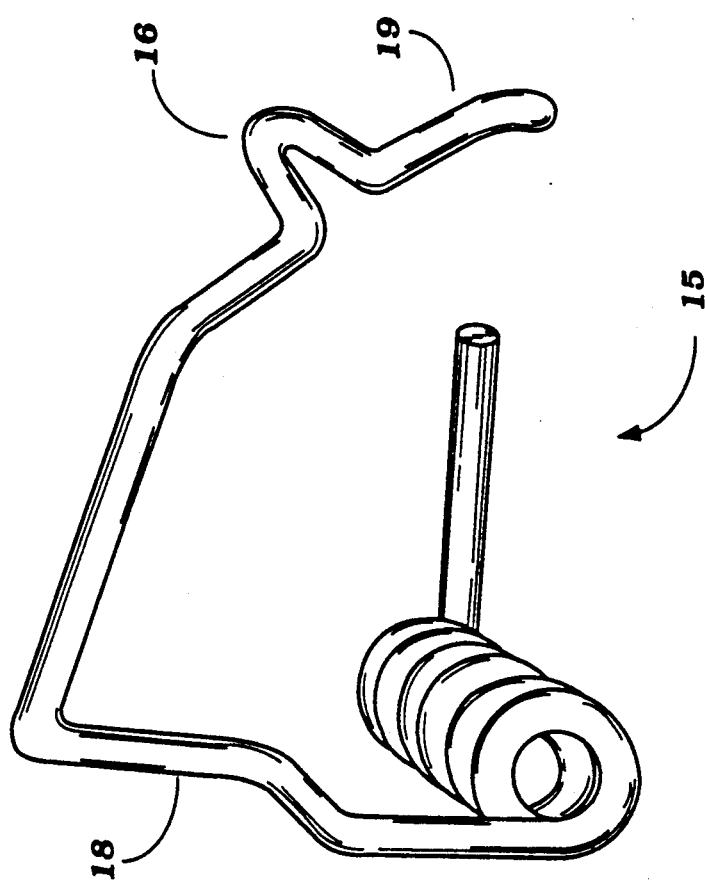
FIG. 8 is an isometric drawing of one possible secondary spring for the tip responsive guard.

The preferred embodiment of the tip responsive guard also employs a component which could take on a variety of shapes, the ultimate choice also depending on the outcome of a detailed analysis. That component is a secondary spring 15 which for purposes of description can be assumed to be a wire formed coil spring as shown in FIG. 8.

Figure 9:
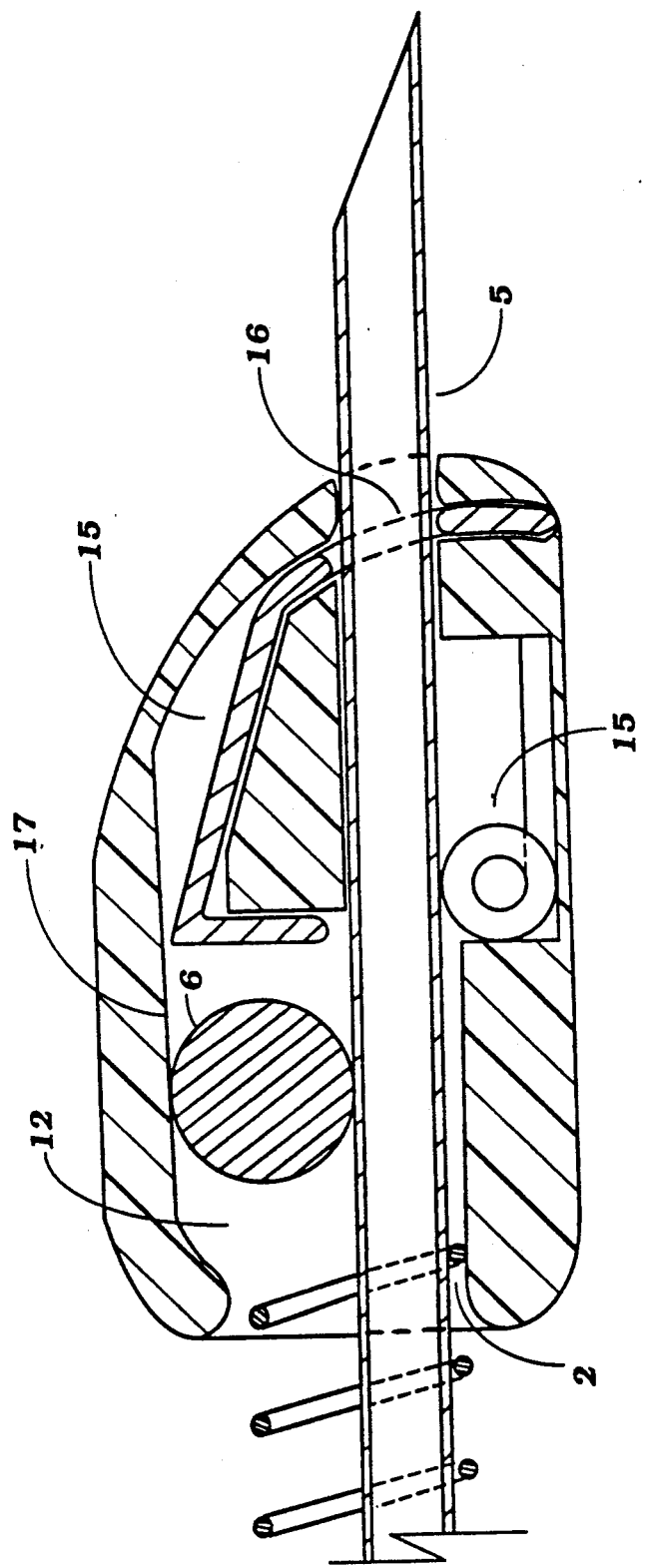
FIGS. 9, 10 and 11 are side view center line cross sections of the tip responsive guard at various stages of operation.

The spring can be seen in the center line cross section of FIG. 9 being held from releasing by the tail loop 16 around the needle shaft 5. The guard is held in place by wedged ball 6. The wall 17 of guard back chamber 12 is slightly tapered inward from front to back thus allowing the ball to be jammed between the wall and the needle. Any attempt to pull the guard off causes the ball to be jammed even more as in a oneway clutch. Also jammed against the needle is the first coil of spring 2.

Figure 10:
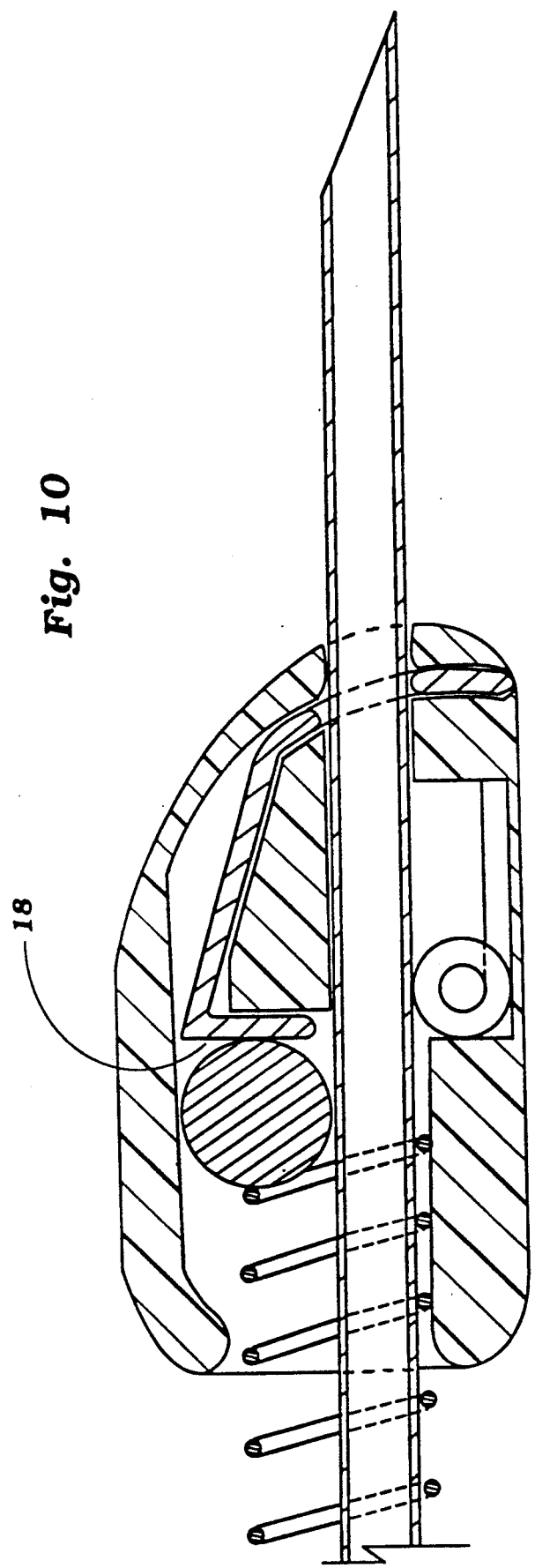

As shown in FIG. 10 forced movement of the guard away from the tip due to needle insertion causes the ball to roll counterclockwise. For each increment of distance back from the tip that the guard is moved, the ball moves half that distance. This means that relative to the guard the ball is moving toward the front and therefore out of its jammed relationship with the guard and needle. When this occurs the pressure against the first coil of the spring is relieved and the spring becomes free to push the ball against secondary spring arm 18. As the needle is withdrawn the primary coil spring pushes the entire mechanism toward the needle tip. This movement cannot cause the ball to become jammed again because now the primary coil spring is keeping the ball against the secondary spring arm and away from that portion of the back chamber where jamming occurs.

Figure 11:
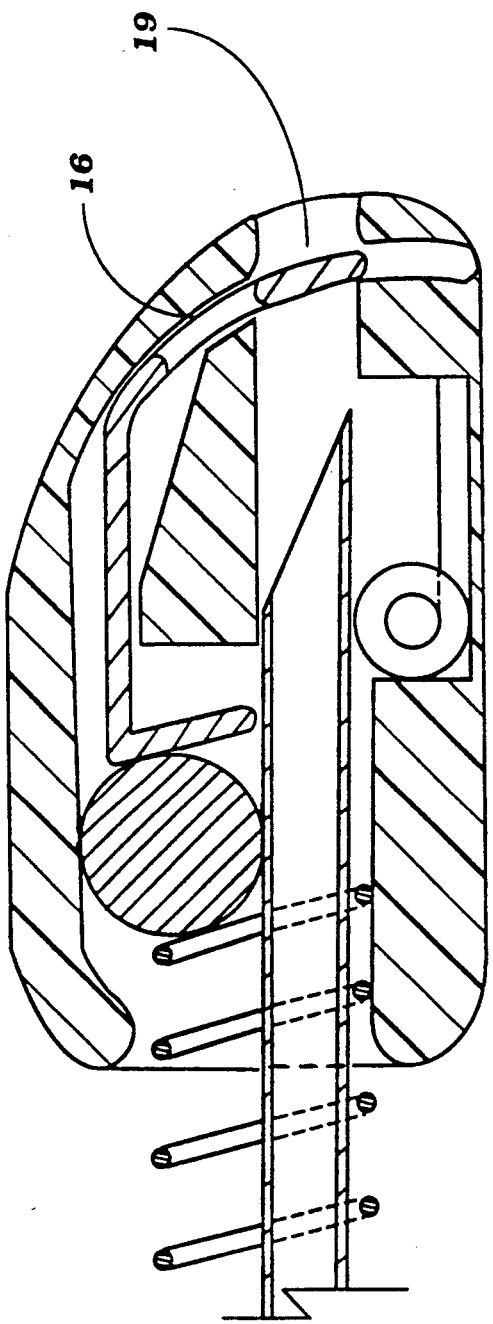

In FIG. 11 the guard has been pushed beyond the needle tip. As soon as the tip clears the secondary spring loop 16, the secondary spring is released. The spring tail 19 then blocks the needle's exit and, since the secondary spring force is greater than the primary coil spring force, the ball is forced back into a jammed relationship between the guard and needle. As the ball comes back into contact with the guard wall while the guard is still moving forward any rolling of the ball will cause the ball to move rearward relative to the guard and therefore into tighter jamming. The guard becomes locked on the end of the needle. It can be pushed back slightly until the tip hits the spring tail, but the secondary spring keeps the ball in its jammed position so that any attempt to pull the guard off also results in even tighter jamming. The guard can be designed such that even if the occluding secondary spring tail is bent the needle cannot penetrate the guard because there won't be enough space for both the needle tip and spring tail to exit at the same time. So only the presence of a portion of the tail is necessary to successfully entrap the needle tip. This along with other design factors allows the entire length of the back chamber to be available for jamming. This is important because manufacturing variations and temperature changes, etc., may cause the ball to jam at slightly different locations.

An alternative flat spring steel secondary spring configuration is shown in FIG. 12. The tail loop has been replaced by a tail hole 20. The needle also passes through a rear hole 21 in rear plate 22. The rear hole can be made just slightly larger in diameter than the needle such that the spring can bind to the needle after it is released. While the rear plate is at right angles to the needle prior to release in the same manner as spring arm 18 of FIG. 10, it changes angles after release as in FIG. 11 and can bind on the needle. This binding can hold the guard on the needle and also pull the jammed ball into even tighter jamming should there be an outside force attempting to pull the guard off the needle. An engineering analysis would be required to determine which spring configuration would be optimum for this application.

What is claimed is:

1. An automatically activated guard for the tip of a one-time use standard hypodermic needle comprising:
    a standard disposable hypodermic needle having a pointed tip at the front and attached to a standard hub at the rear; and
    a hollow needle tip guard through which said needle passes, said guard being initially located near said tip; and
    a ball inside said guard; and
    an anchor wire extending from an anchor point on said needle hub to an anchor point on the inside of said guard; and
    a stop attached to said anchor wire between the two anchor points and wedged between said ball and said needle in front of said ball; and
    a partially compressed coil spring extending from said needle hub to said ball, said needle passing longitudinally through said coil spring, said needle tip guard having an inner chamber of two portions, the rear portion containing said ball and having a rear opening large enough for said coil spring to pass therethrough but too small to allow passage of said ball, the front portion being large enough to allow passage of said stop from in front of said ball to the rear of said ball, said inner chamber having a constriction between said rear portion and said front portion large enough for said ball to pass therethrough but too small to allow passage of said stop from in front of said ball to the rear of said ball, said guard having a front opening large enough to allow passage of said needle but too small to allow passage of said ball therethrough, said ball being movable by said coil spring to a position at the front of said inner chamber occluding said front opening, said guard being movable by said coil spring to a position enclosing said needle tip, and said anchor wire being of such a fully extended length that travel of said guard rear opening beyond the front of said needle tip is prevented.

2. An automatically activated guard for the tip of a one-time use standard hypodermic needle comprising:
    a standard disposable hypodermic needle having a shaft with a cylindrical surface and a pointed tip at the front and attached to a standard hub at the rear; and
    a hollow needle tip guard having a front opening and a rear opening and through which said needle passes, said guard being initially located near said tip; and
    a ball inside said guard; and
    a partially compressed coil spring extending from said hub to said guard, said needle passing longitudinally through said coil spring; and
    a tensioned secondary spring located inside said guard in front of said ball, said secondary spring being held from release by said needle shaft and having a spring force greater than the spring force of said coil spring, said guard having an inner chamber defining an inner wall, that portion of said chamber in which said ball is located having an inner wall portion which tapers from front to back, the dimension from said needle surface to said wall portion at the front of said chamber portion being slightly greater than the ball diameter and the dimension from said needle surface to said wall at the back of said chamber portion being slightly less than the ball diameter, said ball initially being wedged between said wall portion and said needle shaft, the front coil of said coil spring initially being wedged between said needle shaft and that portion of said guard inner wall lying on the opposite side of said needle shaft from said ball, said ball being movable by said coil spring to a position in which it is in contact with the rear portion of said secondary spring, said tensioned secondary spring being releasable by the absence of said needle shaft at the front of said secondary spring, the rear portion of said secondary spring being movable in contact with said ball to a position at which said ball is wedged between said tapered wall portion and said needle shaft, the front portion of said secondary spring being movable to a position occluding said guard front opening, and said guard being movable by said coil spring to a position enclosing said needle tip.

3. The guard of claim 2 in which the secondary spring is a wire formed coil spring and the front and rear portions of said secondary spring are an extension of the coil wire.

4. The guard of claim 2 in which the secondary spring is formed from spring steel sheet, said secondary spring having a hole in the rear portion for the needle to pass therethrough.

5. The secondary spring of claim 4 in which the hole in the rear portion of said secondary spring is large enough to allow needle shaft passage therethrough without binding while said spring rear portion is substantially perpendicular to the needle shaft, but too small to allow needle shaft passage therethrough without binding while said spring rear portion is substantially angled relative to the needle shaft.

* * * * *